United States Patent [19]

Eisele et al.

[11] Patent Number: 5,786,235
[45] Date of Patent: Jul. 28, 1998

[54] PROCESS FOR DEPOSITING A SURFACE-WIDE LAYER THROUGH A MASK AND OPTIONALLY CLOSING SAID MASK

[75] Inventors: Ignaz Eisele, Icking; Bertrand Flietner, München; Josef Lechner, Bad Aibling, all of Germany

[73] Assignee: Siemens Aktiengesellschaft, Munich, Germany

[21] Appl. No.: 537,915

[22] PCT Filed: May 5, 1994

[86] PCT No.: PCT/DE94/00505

§ 371 Date: Oct. 31, 1995

§ 102(e) Date: Oct. 31, 1995

[87] PCT Pub. No.: WO94/25863

PCT Pub. Date: Nov. 10, 1994

[30] Foreign Application Priority Data

May 5, 1993 [DE] Germany ............ 43 14 888.3

[51] Int. Cl.[6] ............ H01L 21/44; H01L 21/465
[52] U.S. Cl. ............ 438/53
[58] Field of Search ............ 437/182, 228 SEN, 437/901, 921, 927; 148/DIG. 73, DIG. 159; 257/415, 416, 419; 438/50, 51, 52, 53

[56] References Cited

U.S. PATENT DOCUMENTS

| | | | |
|---|---|---|---|
| 4,262,399 | 4/1981 | Cady | 257/416 |
| 4,411,741 | 10/1983 | Janata . | |
| 4,469,719 | 9/1984 | Martin . | |
| 5,262,000 | 11/1993 | Wellbourn et al. | 437/182 |
| 5,393,375 | 2/1995 | MacDonald et al. | 437/241 |
| 5,510,276 | 4/1996 | Deim et al. | 437/901 |
| 5,573,679 | 11/1996 | Mitchell et al. | 216/2 |

FOREIGN PATENT DOCUMENTS

| | | |
|---|---|---|
| 241536 | 7/1965 | Austria . |
| 0 341 964 | 11/1989 | European Pat. Off. . |
| 027798 | 3/1964 | Germany . |
| 38 34 189 | 2/1990 | Germany . |
| 42 39 319 | 4/1993 | Germany . |

Primary Examiner—Brian Dutton

[57] ABSTRACT

As a result of deposition from different directions through a mask, a layer can be applied last in a surface-wide form underneath the mask. In this arrangement, the mask is separated by a cavity from the base in the coating region and is firmly joined to it outside the coating region. This process is advantageous, in particular, for the SGFET (suspended-gate field-effect transistor) used as gas sensor. In this process, the mask also forms the gate and the sensitive layer is not subjected to any further process after the deposition. The mask may then remain open or be closed by depositing such a large amount that the openings in the mask are grown over laterally, or by depositing an additional layer at an oblique angle. This process is also suitable for producing micromechanical membranes.

29 Claims, 4 Drawing Sheets

FIG 8
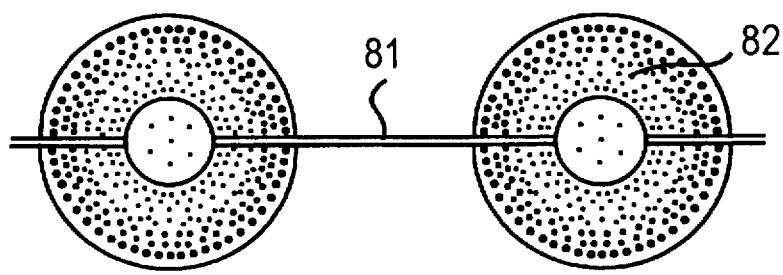
FIG 9A
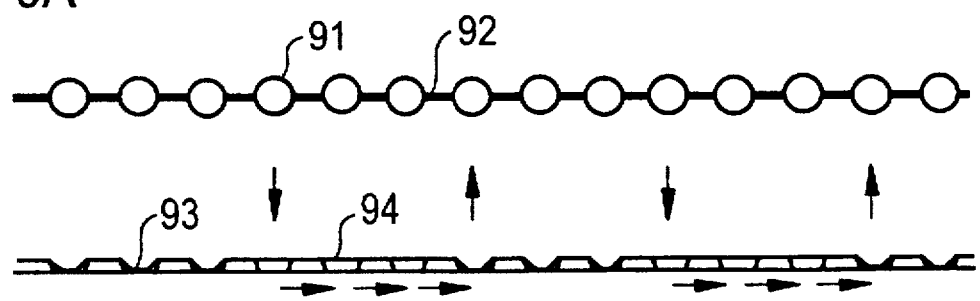
FIG 9B

PROCESS FOR DEPOSITING A SURFACE-WIDE LAYER THROUGH A MASK AND OPTIONALLY CLOSING SAID MASK

This application is a 35 U.S.C. 371 application PCT/DE94/00505, filed on May 5, 1994.

BACKGROUND OF THE INVENTION

The invention relates primarily to the improvement of the SGFET (suspended-gate field-effect transistor) as a gas sensor, but it also has other possible applications, such as the production of microscopic capillaries and micromechanical membranes. The prior art relevant to structuring with the aid of masks during vapor deposition is disclosed in prior art references Austrian Patent 241,536, German Patent 027,798 and U.S. Pat. No. 4,469,719.

In the SGFET (U.S. Pat. No. 4,411,741), the sensitive layer can be deposited either electrochemically or by physical methods (German Patent 3,834,189) such as sputtering or vapor deposition. Since the sensitive layer must be situated between the gate and the channel of the transistor, other processing steps such as the production of the gate or the etching of the spacer follow the application of the sensitive layer by physical methods. These steps may alter the sensitive layer, or only a few materials are compatible with these subsequent steps. This narrows down the choice of the sensitive layer considerably.

SUMMARY OF THE INVENTION

The object is to produce an integrable SGFET whose chemically sensitive layer is not altered by any further processing step.

In general terms the present invention is a process for producing a suspended-gate field-effect transistor. A gate oxide is applied to a substrate which comprises a source region, a drain region and a channel disposed in between. A first silicon nitride layer, a silicon dioxide layer, a second silicon nitride layer and a metal layer are applied to the gate oxide. The metal layer and the second silicon nitride layer are structured using a photoresist procedure such that a mask is produced. A cavity is formed beneath the mask by etching the silicon dioxide layer in an etching process which attacks silicon dioxide selectively with respect to silicon nitride and metal. A chemically sensitive layer is deposited underneath the mask. The deposition of the chemically sensitive layer takes place from different directions so that a surface-wide coating takes place underneath the mask. The mask forms, a gate electrode or membrane, a functional component of the suspended-gate field-effect transistor.

In an advantageous development the mask is closed during the deposition of the layer.

Another embodiment of the present invention is also a process for producing a suspended-gate field-effect transistor. A gate oxide is applied to a substrate which comprises a source region, a drain region and a channel disposed in between. A first silicon nitride layer, a silicon dioxide layer, a second silicon nitride layer and a metal layer are applied to the gate oxide. The metal layer and the second silicon nitride layer are structured with the aid of a photoresist procedure so that a mask is produced. A cavity is formed underneath the mask by etching the silicon dioxide layer in an etching process which attacks silicon dioxide selectively with respect to silicon nitride and metal. A chemically sensitive layer is deposited underneath the mask. The deposition of the chemically sensitive layer takes place from different directions so that a coating over the entire area takes place underneath the mask. The mask is closed by a deposition. The mask forms, as gate electrode or membrane, a functional component of the suspended-gate field-effect transistor.

Advantageous developments of the present invention are as follows.

A grid is used as the mask.

A layer with honeycomb structure is used as the mask.

Part of a gas sensor is used as the coated area.

The sensitive layer of a gas sensor is used as the coated area.

A part of a gas sensor whose principle of measurement is based on a change in work function during gas adsorption is used as the coated area.

The area on which the layer is deposited was already structured.

Sensitive elements, such as conductivity or capacity structures, have already been produced on the area on which the layer is deposited.

The channel of a transistor has already been produced below the area on which the layer is deposited.

After the cavity has been closed, an adhesive or a liquid which hardens is applied without capillary effects occurring.

The transistor produced by the process is used as a pressure sensor or part of a pressure sensor.

The suspended-gate field-effect transistor produced by the process is used as a microphone or part of a microphone.

The suspended-gate field-effect transistor produced by the process issued as a detector for the photoacoustic effect.

The suspended-gate field-effect transistor produced by the process is used as an acceleration sensor or part of an acceleration sensor.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures of which like reference numerals identify like elements, and in which:

FIG. 8 depicts a lateral structure of two pump or valve pieces connected by a microcapillary; and FIG. 9A depicts the lateral structure of a an active gas line; and FIG. 9B depicts a cross-section through the FIG. 9A active gas line.

DESCRIPTION OF THE PREFERRED EMBODIMENTS

As a result of the method proposed here of depositing through the mask which also forms the gate, all those materials can be used as the sensitive layer which can be applied by directional deposition such as sputtering or vaporization. These layers do not have to be compatible with any etching step since the sensitive layer is applied last.

Figure 1:
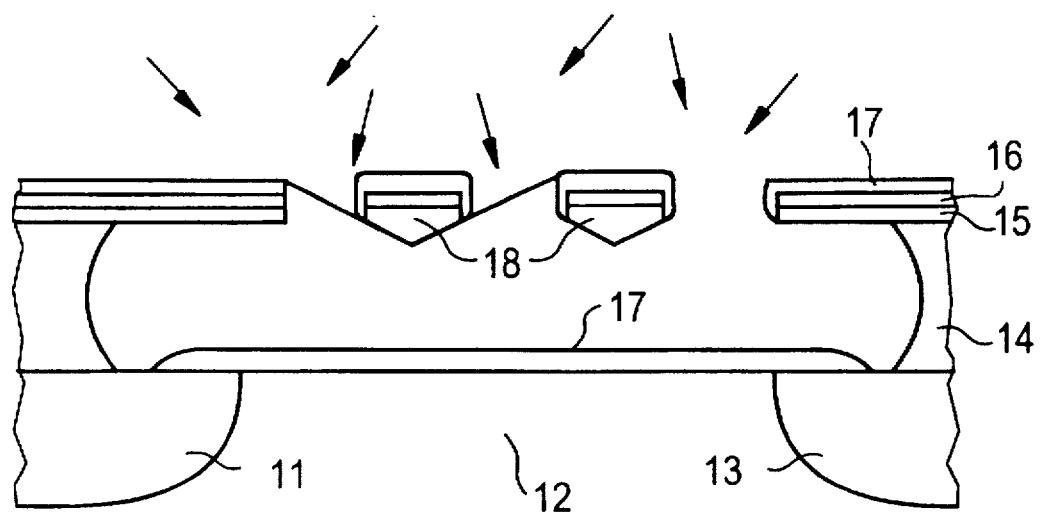
FIG. 1 shows diagrammatically an SGFET which permits the novel process of depositing the chemically sensitive layer according to the present invention.

FIG. 1 shows diagrammatically an SGFET which permits the novel process of depositing the chemically sensitive layer. A thin layer of silicon dioxide is situated above the channel (12) between source (11) and drain (13) and a thin layer of silicon nitride (not shown in greater detail in the figure) is situated on top thereof. Silicon dioxide (14) is deposited thereon, then silicon nitride (15) and, finally, metal (16). The metal forms the gate and the nitride layer is a passivation of the lower metal surface. This is expedient in order to measure, if possible, only the response of the sensitive layer with the sensor since the latter basically indicates the change in the work function difference of the materials above and below the cavity. A photoresist step is then carried out so that an etching through of the nitride/metal layer can take place in a structured manner. After this step, the thick oxide layer is wet-chemically etched through the holes in the mask and the silicon dioxide above the channel region of the transistor is thus removed. The nitride layer and the metal (for example, platinum) are not etched during this process. The choice of the nitride/ silicon dioxide layer system ensures the production of a defined cavity since selective etching methods and defined deposition methods are available for this purpose. The chemically sensitive layer (17) can now be deposited on the structure in a final step. In this connection, the web width and the cavity height must be in the same order of magnitude and the web height may have at most the size of the hole width so that the area directly underneath the webs is also covered. Or to express it in other words: the core shadow (18) of the mask parts above the transistor region must not reach down to the substrate.

This novel process for producing the SGFET has the following advantages:

1. The coating is not exposed to any further processing step and is thus no longer altered, or materials can be used which would be destroyed by a further processing step.

2. Materials can be used which are not normally used in semiconductor technology since they would unacceptably contaminate manufacturing plants for processes which would otherwise take place subsequently.

3. Since all the production steps up to the last coating can be identical for different materials, even small numbers of pieces can be produced cost effectively for a particular sensitive material. For a gas sensor, there are two expedient connections to the gas volume to be measured. Firstly, as short as possible a gas inlet with large cross section in order to expose the sensor quickly to the current concentrations. Secondly, a long gas inlet with small cross section in order to obtain a particular, chemisorbed surface coverage of the sensitive layer, to exploit transit-time effects or to be able to connect valves and pumps. Both types of gas inlet are possible with the sensor proposed here. A short gas inlet with large cross section can be implemented by a mask which is left open. The gas volume to be measured starts immediately above the mask. With this technique, a grid mask can also be produced above gas sensors which are based on other methods of measurement, such as, for example, conductivity and capacity sensors with interdigitate structures. This mask then serves as a protection against particles, the maximum size of the particles passing through being set by the hole size.

Figure 2:
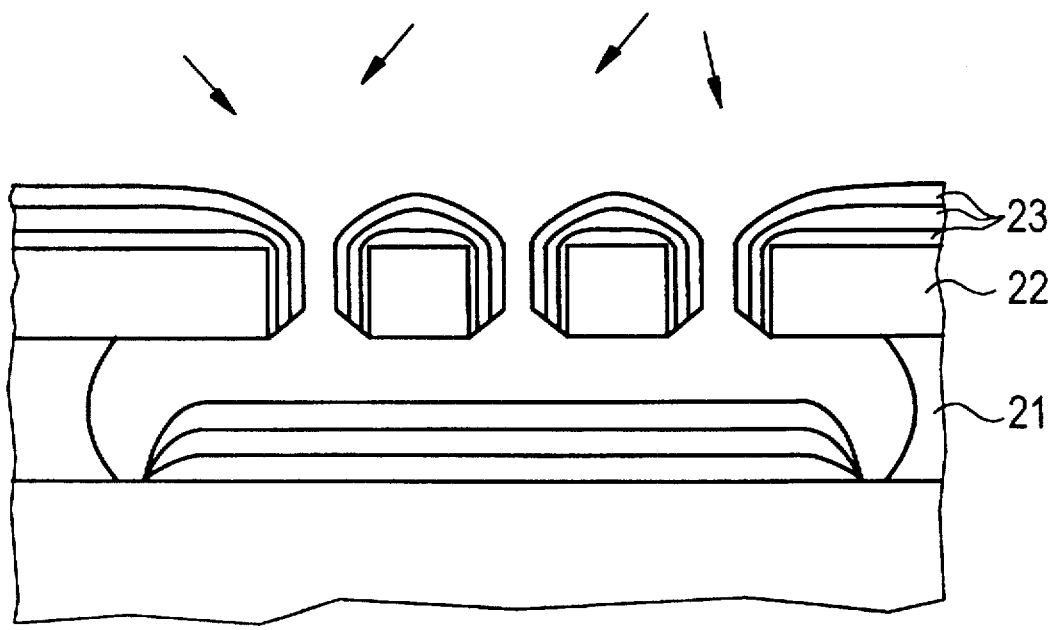
FIG. 2 depicts the application of the sensitive layer.

A long gas inlet with short cross section can be achieved as follows. The mask above the cavity is closed. This can be done by carrying out the application of the sensitive layer relatively isotropically, and in this way, not only is a layer deposited on the insulator above the channel, but the holes in the mask are also slowly overgrown. This is shown in FIG. 2. The silicon dioxide layer (21) etched away in the active region and the nitride/metal layer (22) are produced as described above. Then so much chemically sensitive material (23) is deposited that the holes in the mask are closed. A large web height in proportion to the hole width is conducive to this. Both shadow-free deposition underneath the mask and closure of the holes in one step are possible if not only web width and cavity height but also web height and hole width are each in the same order of magnitude.

Figure 3:
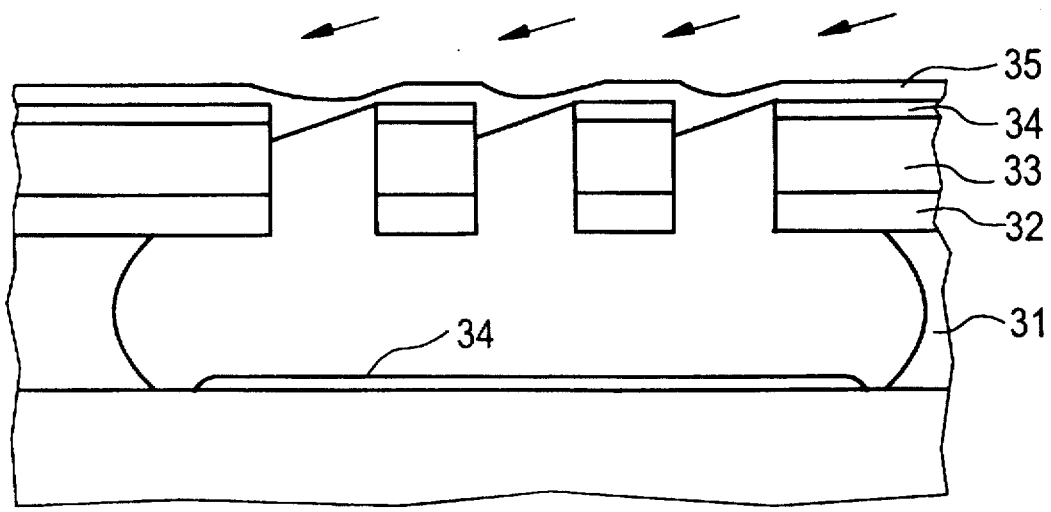
FIG. 3 shows applying material to the mask at an oblique angle in order to close the mask.
Figure 4:
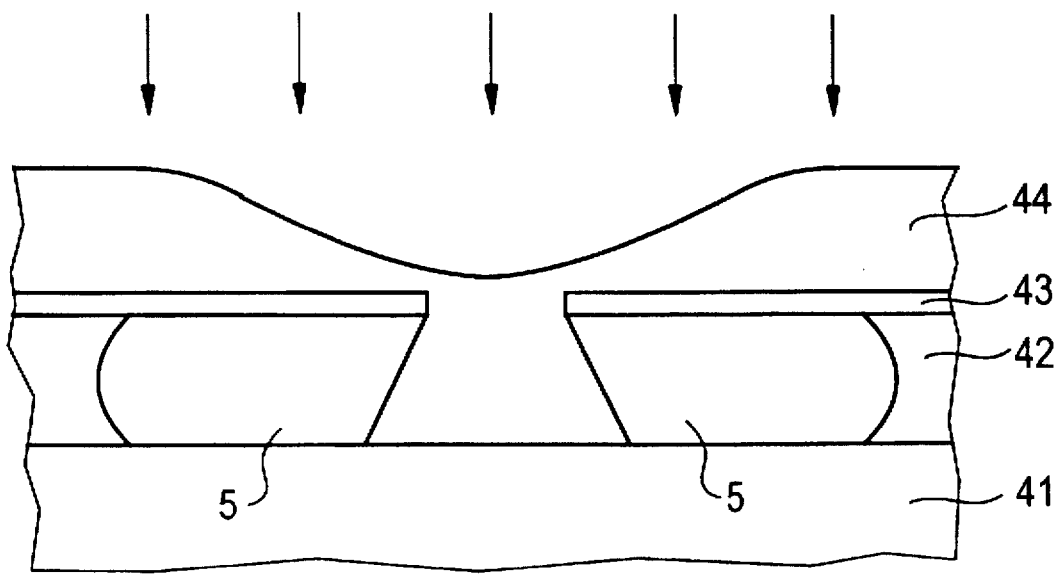
FIG. 4 depicts the vertical structure of a gas channel.
Figure 5:
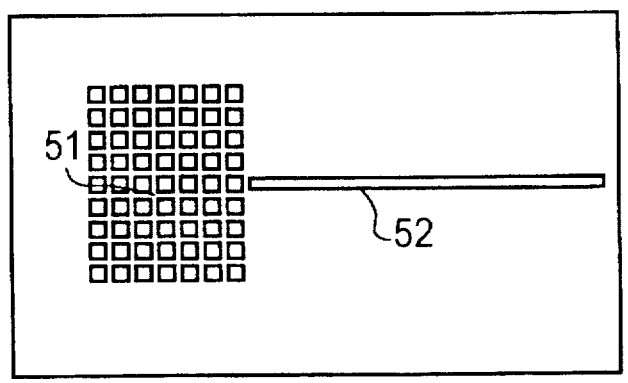
FIG. 5 depicts a structured metal/nitride mask.

The mask may also be closed in an additional step in which a material is applied at such an oblique angle that it is unable to pass through the mask, i.e. is not deposited on the sensitive layer, and thus closes the holes in the mask. This is shown in FIG. 3. The structure arises as described for FIG. 1. It comprises: silicon dioxide (31), nitride (32), metal (33). After the chemically sensitive layer (34), a material (5) is now deposited at a very oblique angle to close the holes. The ideal source for this process is annular. If the source is approximately punctiform, a rotation of the sensor structure in the mask plane is helpful. Regardless of the method by which the mask was closed, adhesive or a liquid which hardens may then be applied as a mechanical or chemical protection. The connection to the gas volume to be measured is carried out in the following way. The metal/nitride mask is structured laterally in such a way (shown in FIG. 5) that gas channels (52) is a gas channel) lead away from the gas volume over the transistor region (51). The vertical structure of such a gas channel is shown in FIG. 4. As already described for the production of the SGFET, a silicon dioxide layer (42) is first deposited on the substrate (41), then a nitride or nitride/metal layer (43) is deposited and the latter is structured. A metal layer is not necessary, but does not interfere and can be applied at the same time in order to minimize the total number of photolithographic steps. After etching out the oxide layer in a wet-chemical manner, so much material (44) is deposited that said material extends from the lower to the upper nitride layer and thus closes the hole in the mask. The gas channels (45) are left. As perpendicular a deposition of the material (44) as possible would be beneficial in this case, but is not necessary if the upper nitride layer (43) has sufficiently severe underetching.

The processes for closing the cavity above the transistor are also suitable for producing gas channels but are, on the one hand, somewhat more complicated since, at that point, the material must not join the lower nitride mask to the upper nitride mask, but, on the other hand, the same processing steps can be applied.

A pressure sensor can also be constructed using this technology. If the cavity is closed without connecting a gas channel, a certain amount of gas is enclosed in said cavity. If the mask has the correct mechanical rigidity, it is bent by the pressure difference between cavity and environment. On the basis of the source-drain current at constant gate voltage, conclusions can be drawn about the distance of the mask from the channel of the transistor and, consequently, about the pressure difference. Such a pressure sensor can also be produced with gas channel and said gas channel can be closed at a defined pressure. In this way, the working range of the sensor can be adjusted.

Figure 6:
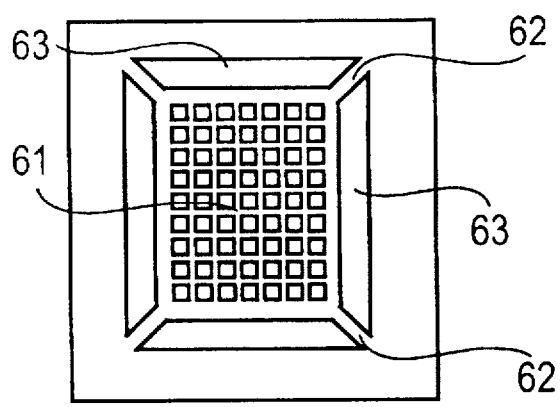
FIG. 6 depicts a transistor region of a nitride mask.

If the gas channel is left open or there are such large holes at the periphery of the transistor region of the nitride mask that they are not closed (FIG. 6: (61) transistor region, (62) remaining webs, (63) holes), the same pressure prevails in the cavity as in the environment. Sound waves which impinge on the mask are able to deflect it and the deflection can be measured with the transistor. In this way, a microphone is obtained.

If a structure such as that for a microphone is screened from the ambient air, it can be used as an acceleration sensor. Because of its inertial mass, the mask is deflected during acceleration of the housing perpendicular to the mask plane and this deflection can be measured as in the case of the pressure sensor and the microphone.

The membranes produced by the novel methods are not only deflected passively, but they can also be actively deflected. For example, there are the following possibilities for doing this:

1. Electrostatically; if both the membrane and the base are electrically conductive and not short-circuited to one another, the capacitor formed by the two surfaces can be charged by applying an electrical voltage between the two. The charges of opposite sign on the two areas mutually attract one another and deflect the membrane towards the base. The membrane can be repelled by the base by charging the two surfaces with the same sign.

2. Magnetically; if the entire actuator is in a magnetic field, for example by providing a permanent magnet, a force acts on a conductor with a current flowing through it on the membrane which can deflect the membrane. Current direction and current level determine along with the magnetic field the direction of the deflection and the amplitude.

3. Thermal stress; if the coefficients of thermal expansion of membrane and base are different, heating or cooling the entire actuator can deflect the membrane. The membrane can also be deflected by generating a temperature difference between base and membrane, for example by heating the membrane with an applied resistance wire. The most promising type of thermal tension is a bimetallic mask, i.e. the membrane itself comprises at least two layers with different coefficients of thermal expansion. The bending of the mask can be adjusted by altering the temperature.

If the two layers having different coefficients of thermal expansion are metals with different Fermi energy, i.e. a contact potential difference is formed, two membranes and a current source can be combined to form a heat pump (Peltier element). Heat energy is thus transported from one membrane to the other at a high efficiency, i.e. one membrane is heated while the other membrane is cooled. The current direction determines which membrane is heated or cooled. If one wishes to activate very many membranes, a variable electrical circuit is beneficial for further optimizing the efficiency. In an electrical circuit, two membrane states should always be connected, each state being capable of being represented by many membranes, to which states the following applies:

1. One state should be heated and one state should be cooled.

2. The temperature of the two membrane states should be as equal as possible.

Figure 7:
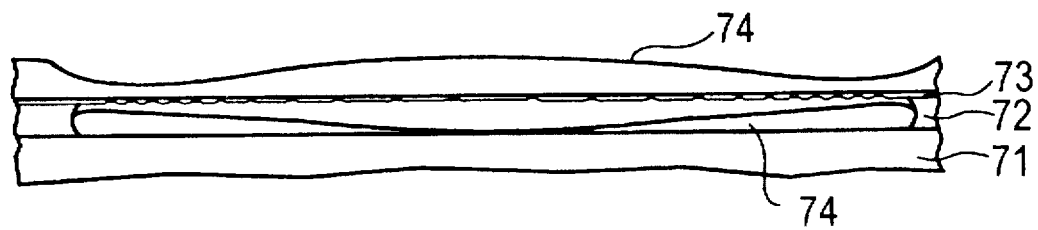
FIG. 7 is a cross-sectional view of a pump or valve piece according to the present invention.

The deflection of the membrane alters the volume of the cavity. If a plurality of such cavities are combined by microcapillaries to form a series, a flow of a liquid through the cavities and capillaries can be achieved by coordinated deflection of the individual membranes. However, with a flat base, the pumping of gases remains difficult since the cavity still has a large dead-space volume even with a membrane bent fully downwards and a backflow remains possible. This problem is solved in the following way. The mask is structured laterally, the openings being varied in size and number over the membrane surface. In combination with the layer deposition for closing the mask, a shape should be produced by this on the base, which shape is the counterpart to the membrane in the lower maximum deflection. FIG. 7 shows such a pump or valve piece in cross section. In this case, (71) is the base, (72) the partially etched-away silicon dioxide layer, (73) the mask with the openings of different size and (74) the material which is deposited to close the mask and which, underneath the mask, has the shape of the bent membrane. The lateral structure of two pump or valve pieces connected by a microcapillary can be seen in FIG. 8 before the closure. In this case, (81) is the microcapillary and (82) is an opening in the mask. Many such pump/valve pieces can be disposed in a row and thus form a pump or an "active gas line". FIG. 9A shows the lateral structure of such an active gas line (91) pump/valve piece, (92) microcapillary) and FIG. 9B shows the cross section through said line (93 bent membrane, 94 membrane in rest position). A sealed gas volume is pushed in a particular direction (horizontal arrows) by coordinated deflection of the membranes (arrow upwards and arrow downwards).

The invention is not limited to the particular details of the method depicted and other modifications and applications are contemplated. Certain other changes may be made in the above described method without departing from the true spirit and scope of the invention herein involved. It is intended, therefore, that the subject matter in the above depiction shall be interpreted as illustrative and not in a limiting sense.

What is claimed is:

1. A process for producing a suspended-gate field-effect transistor, comprising the steps of:
   providing a substrate having a source region, a drain region and a channel disposed between the source region and the drain region;
   applying a gate oxide to the substrate;
   applying a first silicon nitride layer, a silicon dioxide layer, a second silicon nitride layer and a metal layer to the gate oxide;
   patterning the metal layer and the second silicon nitride layer using a photoresist procedure as a mask;
   forming a cavity beneath the mask by etching the silicon dioxide layer in an etching process which attacks silicon dioxide selectively with respect to silicon nitride and metal;
   depositing a chemically sensitive layer underneath the mask from different directions so that a surface-wide coating takes place underneath the mask; and
   the mask forming one of a gate electrode or membrane of the suspended-gate field-effect transistor.

2. The process as claimed in claim 1, wherein the mask is closed during the step of depositing of the chemically sensitive layer.

3. The process as claimed in claim 1, wherein a grid is used as the mask.

4. The process as claimed in claim 1, wherein a layer with honeycomb structure is used as the mask.

5. The process as claimed in claim 1, wherein the part of a gas sensor is used as the coated area.

6. The process as claimed in claim 1, wherein a sensitive layer of a gas sensor is used as the coated area.

7. The process as claimed in claim 1, wherein a part of a gas sensor whose principle of measurement is based on a change in work function during gas adsorption is used as the coated area.

8. The process as claimed in claim 1, wherein the area on which the layer is deposited was already structured.

9. The process as claimed in claim 1, wherein sensitive elements are produced on the area before the layer is deposited.

10. The process as claimed in claim 1, wherein a channel of a transistor is produced below the area on which the layer is deposited and before the layer is deposited.

11. The process as claimed in claim 1, wherein, after the cavity has been closed, an adhesive or a liquid which hardens is applied without capillary effects occurring.

12. The process as claimed in claim 1, wherein the suspended-gate field-effect transistor is a pressure sensor or part of a pressure sensor.

13. The process as claimed in claim 1, wherein the suspended-gate field-effect transistor is a microphone or part of a microphone.

14. The process as claimed in claim 1, wherein the suspended-gate field-effect transistor is a detector for a photoacoustic effect.

15. The process as claimed in claim 1, wherein the suspended-gate field-effect transistor is an acceleration sensor or part of an acceleration sensor.

16. A process for producing a suspended-gate field-effect transistor, comprising the steps of:
providing a substrate having a source region, a drain region and a channel disposed between the source region and drain region;
applying a gate oxide to the substrate;
applying a first silicon nitride layer, a silicon dioxide layer, a second silicon nitride layer and a metal layer to the gate oxide;
structuring the metal layer and the second silicon nitride layer using a photoresist procedure so that a mask is produced;
forming a cavity underneath the mask by etching the silicon dioxide layer in an etching process which attacks silicon dioxide selectively with respect to silicon nitride and metal;
depositing a chemically sensitive layer underneath the mask from different directions so that a coating over the entire area takes place underneath the mask and while closing the mask;
the mask forming one of a gate electrode or membrane of the suspended-gate field-effect transistor.

17. The process as claimed in claim 16, wherein a grid is used as the mask.

18. The process as claimed in claim 16, wherein a layer with honeycomb structure is used as the mask.

19. The process as claimed in claim 16, wherein a part of a gas sensor is used as the entire area.

20. The process as claimed in claim 16, wherein a sensitive layer of a gas sensor is used as the entire area.

21. The process as claimed in claim 16, wherein a part of a gas sensor whose principle of measurement is based on a change in work function during gas adsorption is used as the entire area.

22. The process as claimed in claim 16, wherein the entire area on which the coating is deposited was already structured.

23. The process as claimed in claim 16, wherein sensitive elements are produced on the entire area before the layer is deposited.

24. The process as claimed in claim 16, wherein a channel of a transistor is produced below the entire area on which the layer is deposited and before the coating is deposited.

25. The process as claimed in claim 16, wherein, after the cavity has been closed, an adhesive or a liquid which hardens is applied without capillary effects occurring.

26. The process as claimed in claim 16, wherein the suspended-gate field-effect transistor is a pressure sensor or part of the pressure sensor.

27. the process as claimed in claim 16, wherein the suspended-gate field-effect transistor is a microphone or part of the microphone.

28. The process as claimed in claim 16, wherein the suspended-gate field-effect transistor is a detector for a photoacoustic effect.

29. The process as claimed in claim 16, wherein the suspended-gate field-effect transistor is an acceleration sensor or part of the acceleration sensor.

* * * * *